US00PP14523P29

(12) United States Plant Patent
van Rijn

(10) Patent No.: US PP14,523 P2
(45) Date of Patent: Feb. 10, 2004

(54) ANTHURIUM PLANT NAMED '1999-22'

(50) Latin Name: *Anthurium andreanum*
Varietal Denomination: 1999-22

(75) Inventor: Leonardus W. B. M. van Rijn, Schipluiden (NL)

(73) Assignee: RijnPlant B.V., Schipluiden (NL)

( * ) Notice: Subject to any disclaimer, the term of this patent is extended or adjusted under 35 U.S.C. 154(b) by 0 days.

(21) Appl. No.: 10/377,497

(22) Filed: Feb. 28, 2003

(51) Int. Cl.[7] ..... A01H 5/00
(52) U.S. Cl. ..... Plt./365
(58) Field of Search ..... Plt./365

*Primary Examiner*—Kent Bell
(74) *Attorney, Agent, or Firm*—C. A. Whealy

(57) ABSTRACT

A new and distinct cultivar of Anthurium plant named '1999-22', characterized by its upright and outwardly spreading plant habit; freely clumping growth habit; durable dark green leaves; white, green and dark pink tri-colored spathes with dark pink-colored spadices that are positioned above and beyond the foliage on strong and erect scapes; freely flowering habit; and good inflorescence longevity.

2 Drawing Sheets

Botanical classification/cultivar designation: *Anthurium andreanum* cultivar 1999-22.

BACKGROUND OF THE INVENTION

The present invention relates to a new and distinct cultivar of Anthurium plant, botanically known as *Anthurium andreanum,* and hereinafter referred to by the name '1999-22'.

The new Anthurium is a product of a planned breeding program conducted by the Inventor in Schipluiden, The Netherlands. The objective of the program is to create and develop new compact, freely clumping and freely flowering Anthurium cultivars with strong roots, dark green leaves, attractive spathe color, and good inflorescence longevity.

The new Anthurium originated from a cross by the Inventor on Jan. 6, 1998 of a proprietary selection of *Anthurium andreanum* identified as code number 9608, not patented, as the female, or seed, parent with a proprietary selection of *Anthurium andreanum* identified as code number 9715, not patented, as the male, or pollen, parent. The cultivar 1999-22 was discovered and selected by the Inventor as a plant within the progeny of the stated cross in a controlled environment in Schipluiden, The Netherlands in November, 1999.

Asexual propagation of the new cultivar by meristem culture in a laboratory in Belgium since December, 1999, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 1999-22. These characteristics in combination distinguish '1999-22' as a new and distinct cultivar:

1. Upright and outwardly spreading plant habit.
2. Freely clumping growth habit.
3. Durable dark green leaves.
4. White, green and dark pink tri-colored spathes with dark pink-colored spadices that are positioned above and beyond the foliage on strong and erect scapes.
5. Freely flowering habit.
6. Good inflorescence longevity.

Plants of the new Anthurium can be compared to plants of the female parent, the proprietary selection identified as code number 9608. In side-by-side comparisons conducted in Schipluiden, The Netherlands, plants of the new Anthurium differed from plants of the selection 9608 in the following characteristics:

1. Plants of the new Anthurium had shorter leaves than plants of the selection 9608.
2. Spathes of plants of the new Anthurium were white, green and dark pink tri-colored whereas spathes of plants of the selection 9608 were red and white bi-colored.

Plants of the new Anthurium can be compared to plants of the male parent, the selection 9715. In side-by-side comparisons conducted in Schipluiden, The Netherlands, plants of the new Anthurium differed from plants of the selection 9715 in leaf size as plants of the new Anthurium had larger leaves than plants of the selection 9715.

Plants of the new Anthurium differ primarily from plants of the cultivar Tender Love, disclosed in U.S. Plant patent application Ser. No. 10/377,521 filed concurrently, in spathe and spadix coloration.

Plants of the new Anthurium can also be compared to plants of the cultivar Fantasy Love, disclosed in U.S. Plant Pat. No. 11,771. In side-by-side comparisons conducted in Schipluiden, The Netherlands, plants of the new Anthurium differed from plants of the cultivar Fantasy Love in the following characteristics:

1. Plants of the new Anthurium had smaller, more rounded, glossier and darker green leaves than plants of the cultivar Fantasy Love.
2. Spathes of plants of the new Anthurium were flatter, fleshier, glossier and larger than spathes of plants of the cultivar Fantasy Love.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical flowering plant of the cultivar 1999-22.

The photograph on the second sheet comprises a close-up view of typical inflorescences of '1999-22'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe 10-month old plants grown in 14-cm containers in Schipluiden, The Netherlands, in a glass-covered greenhouse with an average day temperature of 23° C., an average night temperature of 21° C. and light levels about 6 kilolux.

Botanical classification: *Anthurium andreanum* cultivar 1999-22.

Parentage:

*Female parent.*—Proprietary selection of *Anthurium andreanum* identified as code number 9608, not patented.

*Male parent.*—Proprietary selection of *Anthurium andreanum* identified as code number 9715, not patented.

Propagation:

*Method.*—By meristem culture.

*Time to initiate roots on a meristem-cultured plant.*—About 28 days at 24° C.

*Time to develop roots on a meristem-cultured plant.*—About 270 days at 24° C.

*Root description.*—Thick, fleshy, dark pink to cream-colored; lateral roots, abundant.

Plant description:

*Plant shape.*—Upright and outwardly spreading plant habit, narrow inverted triangle, symmetrical.

*Growth habit.*—Freely clumping, bushy and dense growth habit; about nine clumps per plant. Appropriate for 14-cm containers; moderately vigorous.

*Plant height, from soil level to top of leaf plane.*—About 32 cm.

*Plant height, from soil level to top of inflorescences.*—About 37 cm.

*Plant diameter or spread.*—About 37 cm.

*Crop time.*—About 10 months are usually required from planting of young plants to finished plants in a 14-cm container.

*Foliage description.*—Arrangement: Alternate; simple. Quantity per plant: About 45. Length: About 14.7 cm. Width: About 9.3 cm. Shape: Deltoid. Apex: Apiculate. Base: Cordate to truncate. Margin: Entire. Texture, upper and lower surfaces: Leather; glabrous, smooth; durable. Venation pattern: Pinnate. Color: Young leaves, upper surface: More green than 146A. Young leaves, lower surface: 144A to 146B. Mature leaves, upper surface: Slightly more green than 147A. Mature leaves, lower surface: 146B. Venation, upper surface: 144A. Venation, lower surface: 144A to 144B. Petiole: Length: About 21.9 cm. Diameter, just below geniculum: About 4 mm. Diameter, at plant base: About 5 mm. Texture: Smooth. Color: 143B. Geniculum length: About 1.5 cm. Geniculum diameter: About 4.5 mm. Geniculum color: 146A to 147A. Wing length: About 2.8 cm. Wing diameter: About 4 mm. Wing color: 144A to 144B.

Inflorescence description:

*Inflorescence arrangement.*—Spathes with spadices held above and beyond the foliage. Flowering structures arise from leaf axils. Freely and continuous flowering during the autumn in Schipluiden, The Netherlands. Typically about eight inflorescences per plant. Inflorescences not fragrant.

*Inflorescence longevity.*—Inflorescences last about two months under winter conditions and about three months under summer conditions; inflorescences persistent.

*Spathe.*—Length: About 7.7 cm. Width: About 6.3 cm. Shape: Deltoid. Apex: Apiculate. Base: Obtuse. Margin: Entire. Texture, upper and lower surfaces: Leathery; glabrous, smooth. Aspect: Moderately cupped. Color: When opening, front surface: 149D; towards the margins, 144A to 144C. When opening, back surface: 145C; towards the margins, 145A to 145B. Fully developed, front surface: Ground color, close to 155D; towards the base, 143B to 144A; towards the apex, 52B to 52C; venation, 53C to 53D. With development, 143A to 144A; midrib, 53C; towards the apex, 184A. Fully opened, back surface: Ground color, close to 155D; towards the margins, 144A; center and towards the apex, 51C to 52C; venation, 53C to 53D.

*Spadix.*—Length: About 4 cm. Diameter: About 8 mm. Shape: Columnar, tapering towards the apex; apex, obtuse. Cross section: Rounded. Aspect: About 10° from vertical. Color: Immature: 53B to 53C; towards the apex, 180B to 180C. Mature: 51C; towards the apex, 185A.

*Flowers.*—Quantity per spadix: Numerous, about 150. Shape: Rounded. Height: Less than 0.5 mm. Diameter: About 0.8 mm.

*Reproductive organs.*—Androecium: Anther color: 11D. Amount of pollen: Scarce. Pollen color: 11C. Gynoecium: Stigma shape: Ovoid. Stigma color: N155D. Ovary color: N155D.

*Scape.*—Length: About 25.6 cm. Diameter: About 4 mm. Strength: Strong. Aspect: Erect to slightly outwardly slanted, about 30° from vertical. Color: 144A.

*Seed and fruit.*—Seed and fruit development has not been observed on plants of the new Anthurium.

Disease/pest resistance: Under commercial production conditions, plants of the new Anthurium have not been observed to be resistant to pathogens or pests common to Anthurium.

Temperature tolerance: Plants of the new Anthurium have been observed to tolerate temperatures from 14 to 35° C.

It is claimed:

1. A new and distinct cultivar of Anthurium plant named '1999-22', as illustrated and described.

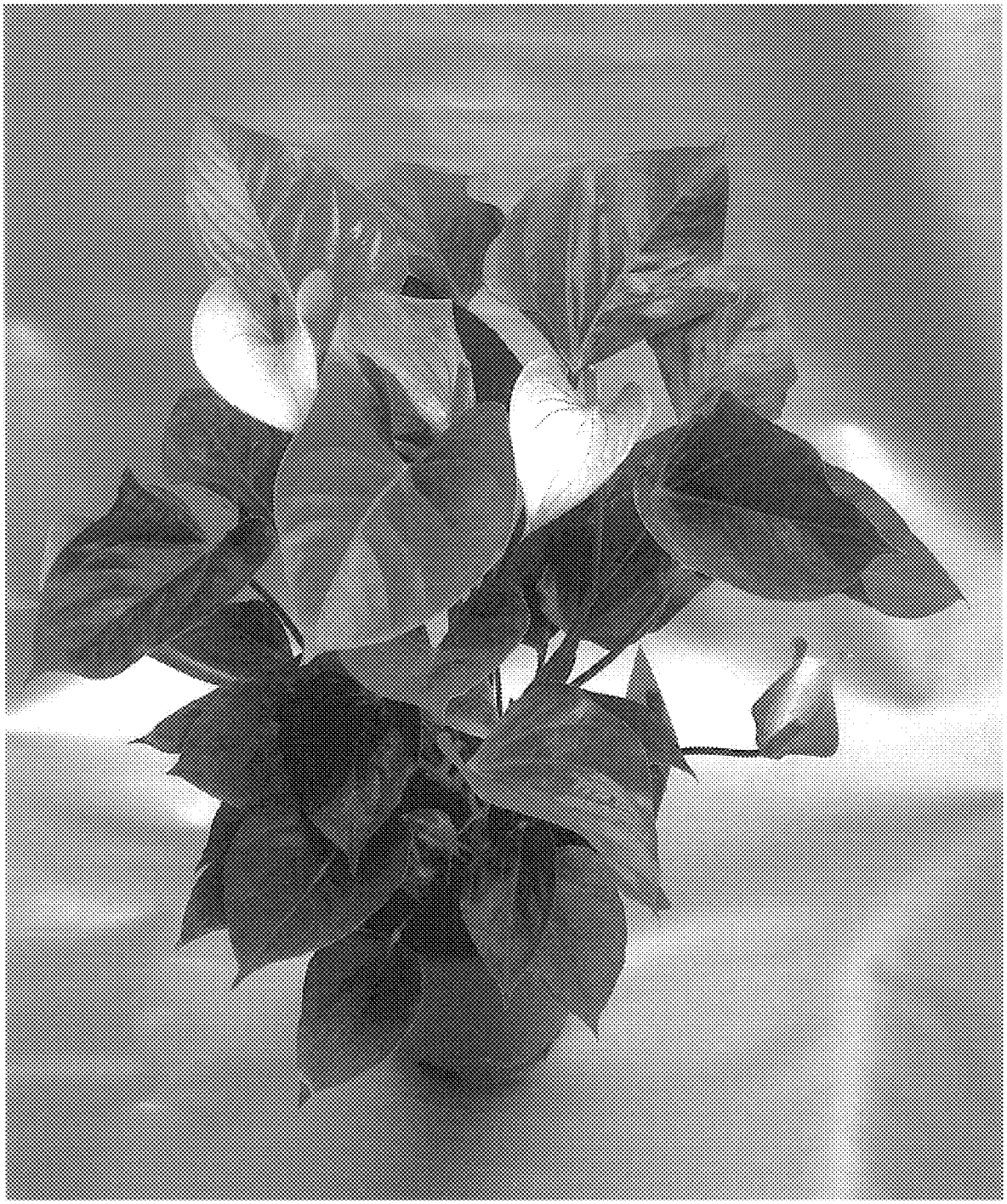

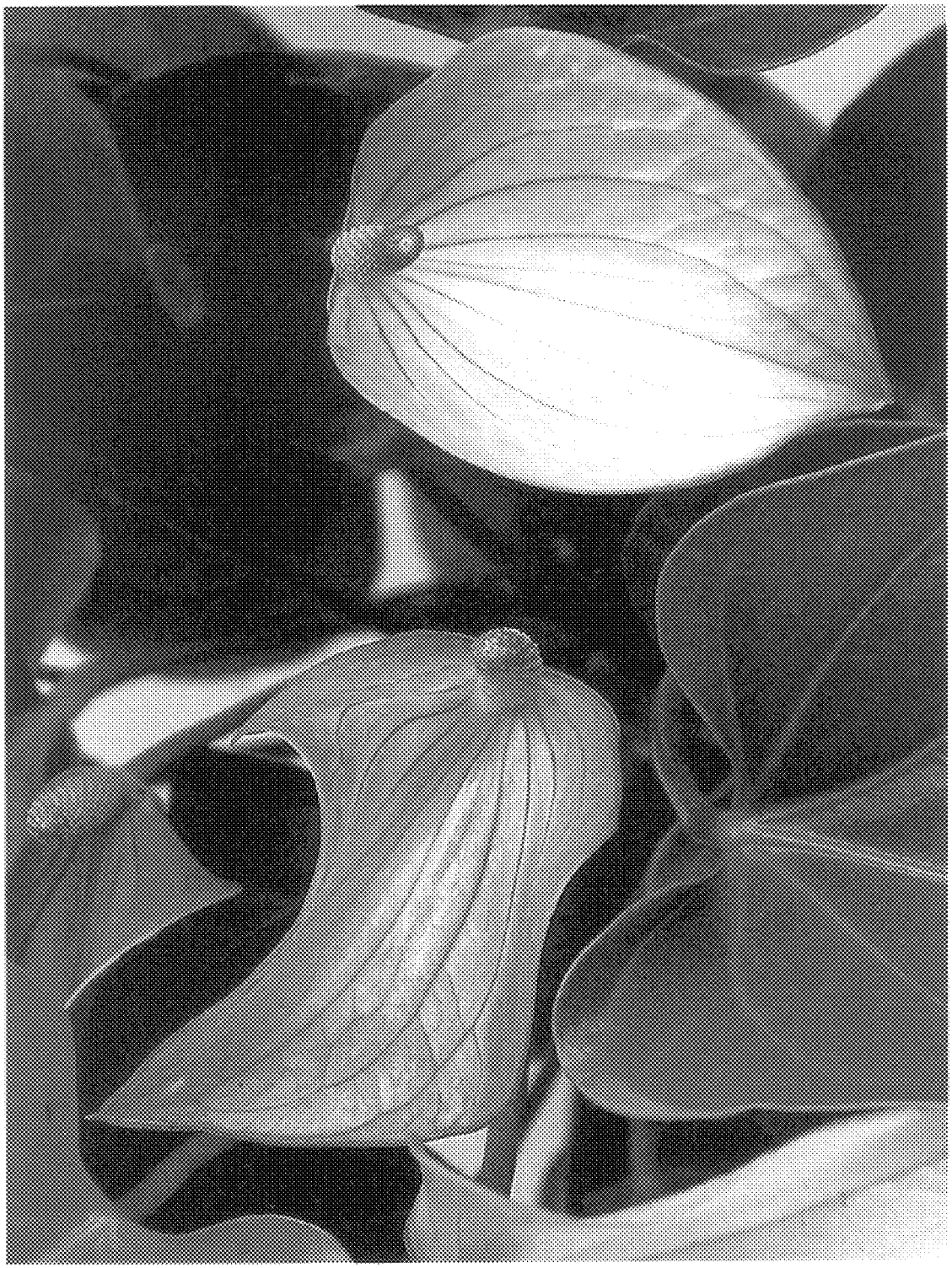

* * * * *